(12) United States Patent
Taylor et al.

(10) Patent No.: US 8,455,816 B2
(45) Date of Patent: Jun. 4, 2013

(54) DETECTION APPARATUS

(75) Inventors: Stephen John Taylor, Hyde Heath (GB); Robert Brian Turner, Chesham (GB); Richard Turner, legal representative, London (GB)

(73) Assignee: Smiths Detection-Watford Limited, Watford (GB)

( * ) Notice: Subject to any disclaimer, the term of this patent is extended or adjusted under 35 U.S.C. 154(b) by 6 days.

(21) Appl. No.: 12/745,324

(22) PCT Filed: Dec. 1, 2008

(86) PCT No.: PCT/IB2008/003801
§ 371 (c)(1),
(2), (4) Date: Dec. 27, 2010

(87) PCT Pub. No.: WO2009/069000
PCT Pub. Date: Jun. 4, 2009

(65) Prior Publication Data
US 2011/0133070 A1    Jun. 9, 2011

(30) Foreign Application Priority Data
Dec. 1, 2007  (GB) ................................. 0723563.3

(51) Int. Cl.
*H01J 49/10*    (2006.01)
(52) U.S. Cl.
CPC ..................................... *H01J 49/10* (2013.01)
USPC ........................................... 250/286; 250/282
(58) Field of Classification Search
USPC ............... 250/286, 287, 281, 282; 73/863.12, 73/863.23
See application file for complete search history.

(56) References Cited

U.S. PATENT DOCUMENTS

| 5,283,199 A * | 2/1994 | Bacon et al. .................. 436/173 |
| 7,141,786 B2 * | 11/2006 | McGann et al. ............... 250/287 |
| 7,299,711 B1 * | 11/2007 | Linker et al. ............... 73/863.23 |

FOREIGN PATENT DOCUMENTS

| WO | WO 2004/102611 A2 | 11/2004 |
| WO | WO 2007/014303 A2 | 2/2007 |
| WO | WO 2007/042763 A2 | 4/2007 |
| WO | WO 20007/113486 A1 | 10/2007 |

OTHER PUBLICATIONS

International Search Report and Written Opinion for International Application No. PCT/IB2008/003801, mail date May 25, 2009, 9 pages.

* cited by examiner

*Primary Examiner* — Kiet T Nguyen
(74) *Attorney, Agent, or Firm* — Foley & Lardner LLP

(57) ABSTRACT

A detection system comprises a housing having a sample inlet and a gas outlet, and a preconcentrator. The preconcentrator can include a microelectromechanical system (MEMS) configured to accumulate or release a dopant at selected times, and can be located inside or outside the housing. The detection system can include an ion mobility spectrometer, a mass spectrometer, or a combination thereof. A method of analyzing a substance comprises supplying a sample gas or vapor comprising the substance, accumulating a dopant in a first preconcentrator, releasing the dopant at selected times from the preconcentrator to an area containing the sample, ionizing the substance to generate detectable species, separating the detectable species, and determining the detectable species by a detection unit. The system and method allow the rapid introduction and removal of dopant to facilitate fast and accurate identification of the sample.

8 Claims, 3 Drawing Sheets

DETECTION APPARATUS

This application claims benefit to United Kingdom Application No. 0723563.3, filed on Dec. 1, 2007, which is hereby incorporated by reference in its entirety.

TECHNICAL FIELD

This application relates to detection systems, and methods of analyzing substances using detection systems.

BACKGROUND

Detection systems, such as ion mobility spectrometers (IMS), mass-spectroscopy, and other detection systems, can use added substance to enhance the detection of target analyte substances. The added substances can be dopants, also know as marker compounds, for example. These will generally be referred to as "dopants." Examples of a detection system using dopants can be found in EP1649274A, PCT/GB06/001739, W006/129101, W007/010,261, PCT/GB06/003677 and PCT/GB07/002,160, each of which is hereby incorporated by references.

In some applications, it is preferable to use one or more dopants at a very low level in order to facilitate a fast removal of the dopants when desired. In some applications, the dopant is added only in particular circumstances, such as when the presence of a particular analyte substance is suspected but not clearly determined. However, it is difficult to add a dopant rapidly, and furthermore, it can take considerable amount of time to remove the dopant when it is no longer needed. Thus, there is a need for improved methods of delivering and removing dopants from detection systems.

SUMMARY

One embodiment provides a detection system comprising a housing having a sample inlet and a gas outlet, and a preconcentrator. The preconcentrator can comprise a microelectromechanical system (MEMS) configured to accumulate or release a dopant at selected times. The detection system can comprise an ion mobility spectrometer, a mass spectrometer, or a combination thereof.

Another embodiment provides a detection system comprising a housing having a sample inlet and a gas outlet and a preconcentrator located inside the housing.

Another embodiment provides a method of analyzing a substance comprising supplying a sample suspected of containing the substance to a housing, accumulating a dopant to a preconcentrator, releasing the dopant at one or more selected times from the preconcentrator to the housing, ionizing the substance to generate detectable species, separating the detectable species, and determining the detectable species by a detection unit. The preconcentrator can be microelectromechanical system (MEMS)

BRIEF DESCRIPTION OF THE DRAWINGS

In FIGS. 1 through 3, solid lines refer to material communications, and doted lines refer to signal communications between the components of the system.

DETAILED DESCRIPTION

Figure 1:
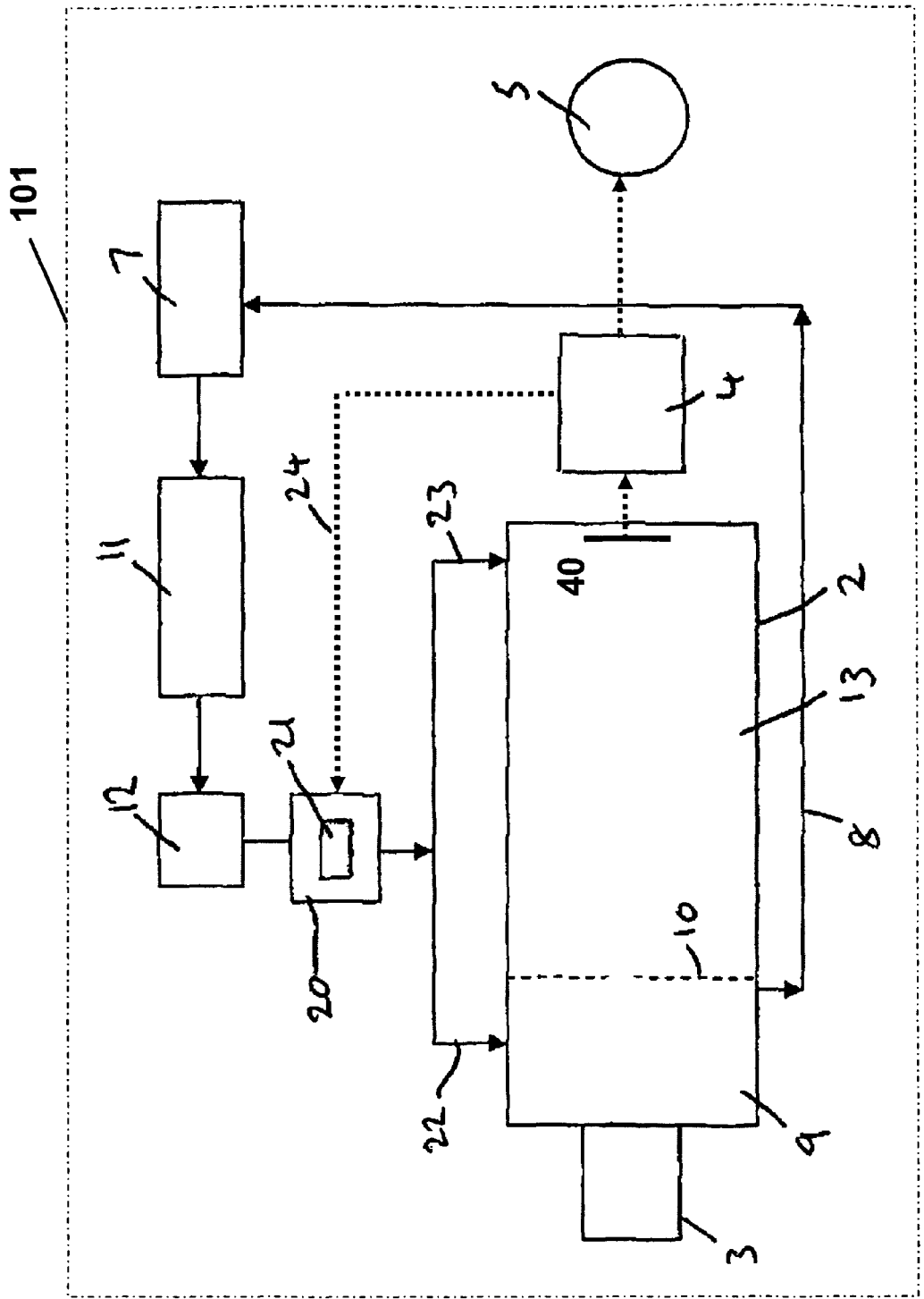
FIG. 1 is an illustrative drawing of a detection system of a first embodiment schematically.

Unless otherwise specified, "a" can refer to one or more. For example, "a dopant" can refer to "one or more dopants" unless otherwise specified.

Unless otherwise specified, the description of one or more components does not preclude additional components. For example, the description of an apparatus including A, B, and C includes an apparatus including A, B, C, and D.

As referred to herein, a "dopant" is any substance used in a detection system to facilitate detection of an analyte. Dopants can include substances introduced into a detection system to generate a known response (also known as a resident ion peak (RIP)). The dopant can be in any physical state, such as a solid, liquid, or gas. Specific dopants can be any suitable reagents, including but not limited to, any suitable substituted or unsubstituted alcohol, ketone, aldehyde, ester, amine, hydrocarbon or organophosphorous compound, which are well-known in the art and vary depending on the particular application. In some embodiments, the dopant is a dopant for use in an ion mobility spectrometer (IMS). In an embodiment, the dopant can be chloromethane.

Generally, a dopant can be added to a detection system, such as an IMS, to modify the ion-molecule reaction chemistry. More specifically, a dopant can be added to prevent ionization of molecules having low electron or low proton affinity, and thus reduce the probability of false positive results. A dopant also can be added to shift one or more interfering ion peaks in the spectrum away from a peak indicating the analyte of interest. By adding one or more dopants to the system, identification and quantification of an analyte of interest can be optimized. Other detection systems, such as, for example, mass spectrometers, also can use dopants to optimize or enhance detection of an analyte of interest.

Exemplary IMS systems are described in, for example, UK Patent Nos. 2324407, 2324875, 2316490, and 2323165, U.S. Pat. Nos. 4,551,624, 6,459,079, 6,825,460, and 6,495,824, and PCT International Application Publication No. WO 2004/102611, and US, which are hereby incorporated by references.

I. Detection Systems

In one embodiment, the application provides a detection system comprising a housing having a sample inlet and a gas outlet and a preconcentrator. The detection system can include an ion mobility spectrometer, a mass spectrometer, or a combination thereof. The detection system can be used to detect any detectable substance such as, for example, explosives, drugs, blister agents, nerve agents, or biowarfare agents. In some embodiments, the detection system can comprise a one or more preconcentrators, which can accumulate and release one or more dopants.

A preconcentrator can be configured to accumulate or release a dopant in response to a stimulus, such as for example, at one or more selected times or a received signal. For example, the preconcentrator can be operated to release a dopant at regular intervals or it can be operated to release dopant in response to a detection output. In some embodiments, the preconcentrator releases dopant at regular intervals and also releases either the same or different dopant in response to a particular detection output.

Any suitable preconcentrator can be used. In one embodiment, the preconcentrator can comprise a MEMS preconcentrator, for example. Exemplary MEMS preconcentrators are described in Tian et al., "Microfabrication Preconcentraion—Focus for a Microscale gas chromatograph", *Journal of Microelectromechanical Systems,* 12(3), p. 264-272 (2003), and Bae et al., "A Fully-integrated MEMS Preconcentrator for Rapid Gas Sampling", IEEE 2007, Lyon, June 1-14, p. 1497-1500 (2007), each of which is hereby incorporated by references. An advantage of the MEMS preconcentrator is significantly reduced dead volume and thermal mass as compared to conventional preconcentrators. Nonetheless, non-MEMS preconcentrators also can be used.

One embodiment of a detection system is illustrated in FIG. 1. The detection system 1 comprises a housing 2, a detection unit 40, a processing unit 4, and a display or other output means 5. The detection unit 40 provides data to a processing unit 4. The processing unit 4 processes the data received, and outputs the process data, indicative of the nature of the analyte substance of interest, to a display 5 or other output means.

The housing 2 can include an ionization region 9 and a drift region 13 that can be separated by a gating grid 10. The gating grid can be any suitable grid, such as, for example, a Bradbury Nielson grid. Further, the housing 2 can include a sample inlet 3, a gas outlet connected to a tubing 8, and gas inlets connecting to a tubing 22 and a tubing 23, respectively. As shown in FIG. 1, the gas outlet can be located in the ionization region 9 and adjacent to the gating grid 10.

The housing 2 can operate at a pressure less than or around atmospheric pressure and can contain electrodes (not shown) energized to produce a voltage gradient along the housing 2.

The detection system 1 further can comprise a gas flow system connected to the housing 2. The gas flow system can include a pump 7, a removing means 11, a dopant source 12, and a preconcentrator 21. An inlet of the pump 7 can be connected to the gas outlet of the housing 2 via the tubing 8, and an outlet of the pump 7 can be connected to the removing means 11, which in turn connects with a source unit 12. The removing means can be any means capable of removing at least a portion of dopant from the detection system and can comprise, for example, a sieve pack or any other suitable materials, and is configured to be capable of cleaning gas recirculating to the housing 2, by removing the dopant and/or other impurities including water vapor.

The source unit 12 can be configured to provide one or more dopants (which is referred to collectively as "dopant") at a first level, which can be a level below a minimum level required for a detectable effect on the detection, to the preconcentrator 21. The effect on the detection can be a substantial effect. The dopants can then be accumulated to the preconcentrator 21. The preconcentrator 21, in turn, can release the dopants to the housing 2 at a second level, a level having a detectable or a substantial effect on the detection. The second level is greater than the first level. For example, the second level can be three, five, ten, twenty, fifty, or more time the first level. For sake of clarity, the amount of dopants released as the second level can be less than the total amount of the dopant provided at the first level. In other words, the second level can be greater than the first while dopant remains in the preconcentrator 21. The dopant can be any suitable chemical reagent including but not limited to, for example, any suitable substituted or unsubstituted alcohol, ketone, aldehyde, ester, amine, hydrocarbon or organophosphorous compound. In one embodiments, the dopant can be chloromethane.

The preconcentrator 21 can be configured to be turned on or off by an electrical signal in such a way that when turned on, the preconcentrator 21 releases at least a part of the accumulated dopant as a short burst of vapor into the housing, and, when turned off, the preconcentrator 21 does not release the accumulated dopant. The preconcentrator can have a preconcentration ratio, a ratio of the concentration of the second level to that of the first level, of approximately 2 to 4000, approximately 100 to 1000, approximately 100 to 2000, approximately 100 to 4000, and approximately 400 to 1000.

The preconcentrator 21 also can be configured to release differing amounts of dopant when turned on. The differing levels can be achieved by varying the duration of the burst or the intensity of the burst. The amount of dopant released can depend on the test conditions or final or interim detection results. In some cases, the user of a detection system can manually adjust the level of dopant to be released.

In some embodiments, the electrical signal controlling the preconcentrator can be set to turn on the preconcentrator at regular intervals, such as, for example, every minute or any other suitable time interval, including, for example, after a sufficient amount of the dopant accumulates to the preconcentrator. In some embodiments, the preconcentrator can include a sensor capable of determining the amount or concentration of dopant present. In some embodiments, the processing unit 4 can be arranged to determine the electrical signal turning on or off the preconcentrator, based on an output of the detection unit 40, for example, turning on the preconcentrator only when the detection unit 40 outputs an ambiguous signal that might be resolved by the addition of the dopant.

The preconcentrator 21 can be connected to the housing at any suitable locations. In some embodiments, the preconcentrator 21 can be located in a preconcentrator housing 20, connecting to a central part of the ionization region 9 via a first tubing 22 and to the end of the drift region 13 remote from the inlet 3 via a second tubing 23, as illustrated in FIG. 1. In some embodiments, when the preconcentrator 21 is turned on by the electrical signal 24, it release a short burst of the dopant into its housing 20, and, in turn, into the housing 2 via a first tubing 22 and/or a second tubing 23.

In some embodiments, the detection system can comprise more than one preconcentrators. Each of the preconcentrators can be configured to accumulate and release a corresponding dopant as described above. The preconcentrators can supply one or more dopants and can supply a same dopant or different dopants, and could be connected at the same point or at different points in the system. In these embodiments, by selectively activating different numbers of preconcentrators, the types of dopants and/or the amounts of dopants released to the housing can be varied.

Figure 2:
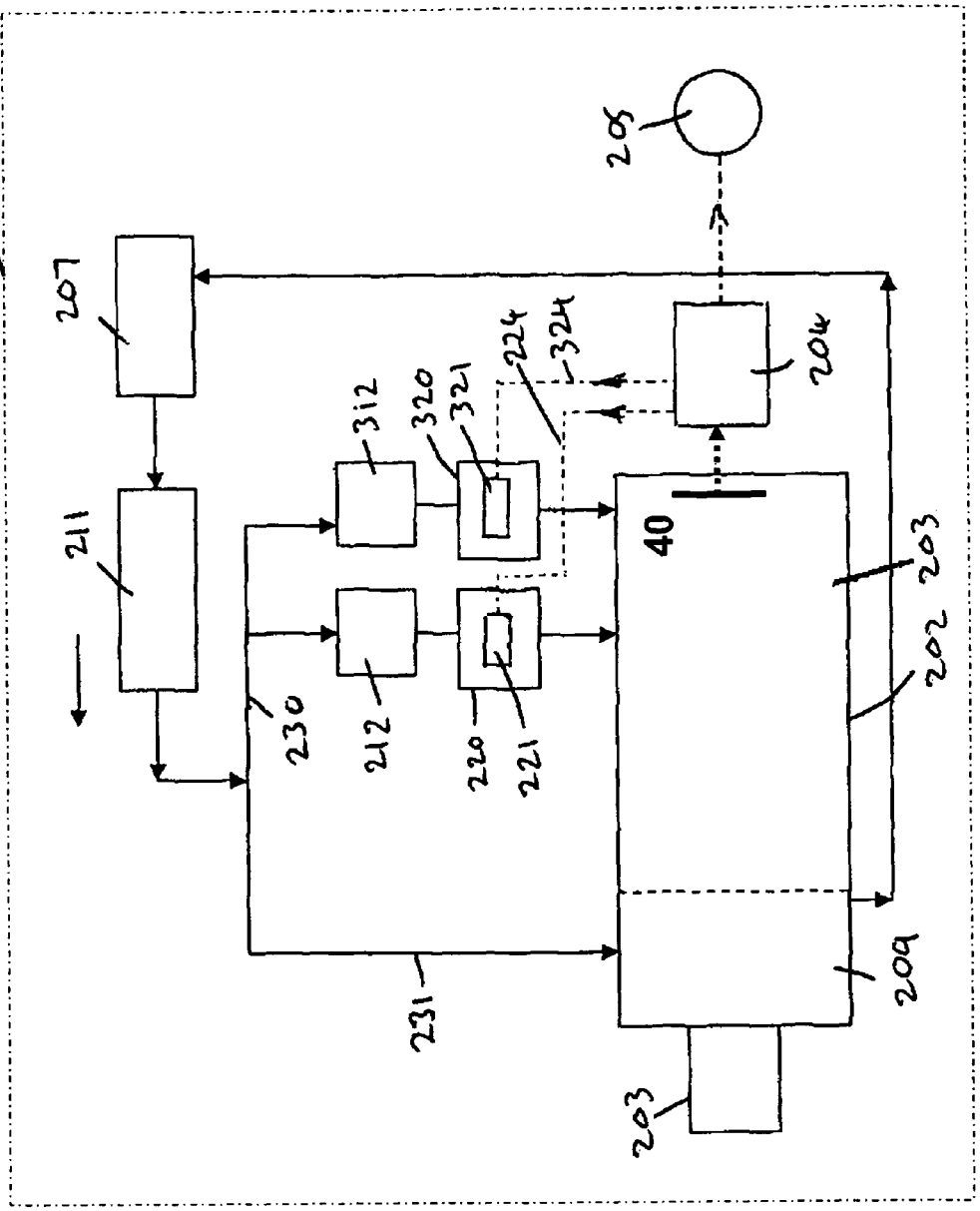
FIG. 2 is an illustrative drawing of a detection system of a third embodiment having more than one preconcentrators.

A non-limiting example of an embodiment is illustrated in FIG. 2. Equivalent components to those in FIG. 1 are numbered using the same numerals with the addition of 200 or 300.

As shown in FIG. 2, the arrangement of the detection system 201 has two source units 212 and 312, connected in parallel to the removing means 211 via a tubing 230. In some embodiments, there only will be one source unit or two or more sources units. The tubing 231 connects the removing means 211 directly to the ionization region 209 of the housing 201. The two source units 212 and 312 can provide a same dopant or two different dopants, to preconcentrators 221 and 321, respectively. The preconcentrators 221 and 321 can be MEMS preconcentrators. The preconcentrators can be located in preconcentrator housings 220 and 320, respectively.

The preconcentrators 221 and 321 can be independently controlled. Thus, in some embodiments, one or the other, or both of the preconcentrators 221 and 321 can be triggered by signals 224 and 324 to release one or more dopants to the housing 202. A single detector unit 40 can readily be switched between two different dopant ion chemistries, which can be dictated, in part, by the generally short-lived nature of the dopant vapor pulses. Any number of preconcentrators can be used, and preconcentrators can be arranged in series instead of in parallel, or in combinations of series and parallel arrangements.

Figure 3:
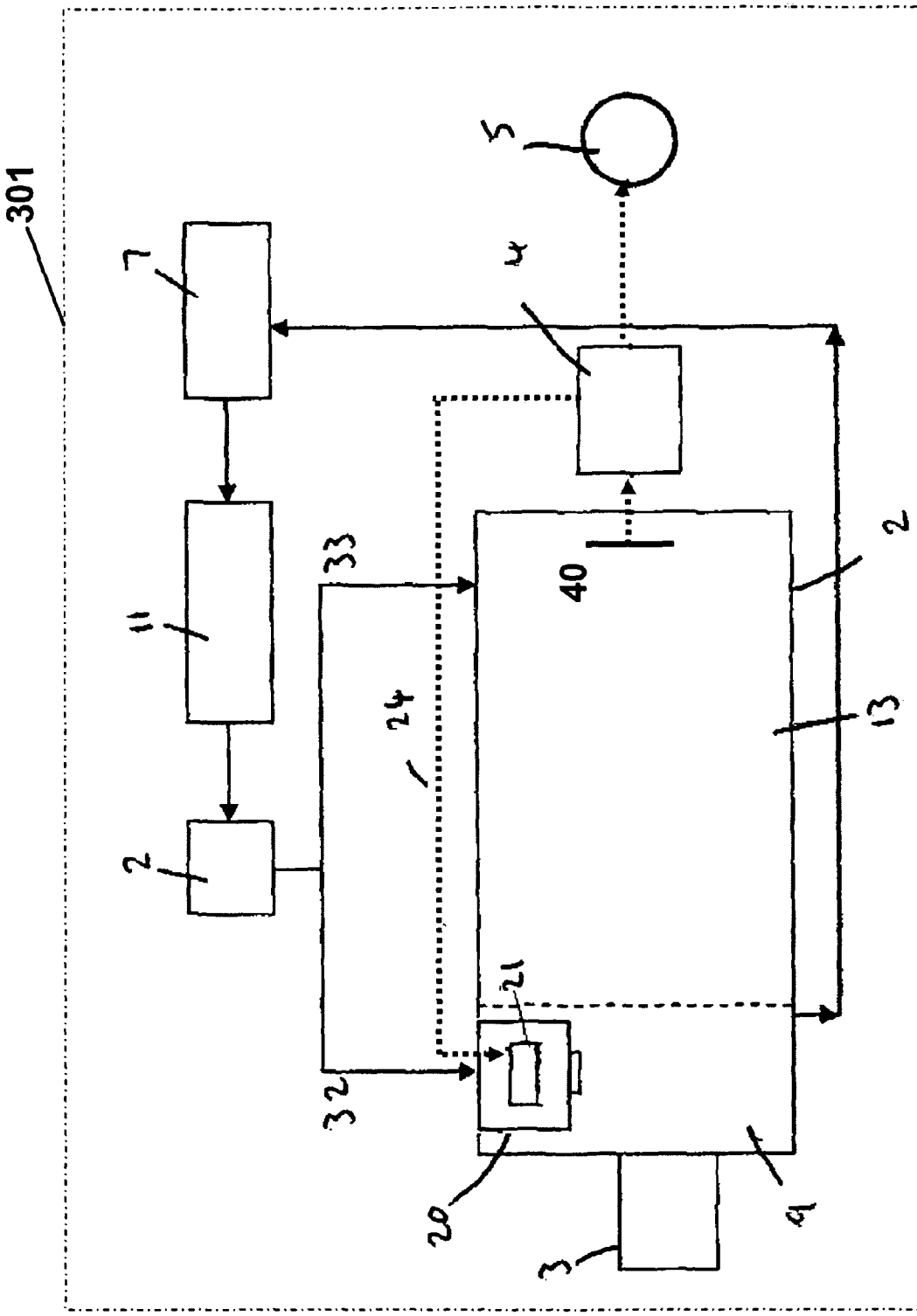
FIG. 3 is an illustrative drawing of a detection system of a second embodiment one or more internal preconcentrators.

Alternatively, one or more preconcentrators can be located inside, rather than being connected via tubing(s) to, the housing. One non-limiting example of these embodiments is illustrated in FIG. 3, in which a preconcentrator 21 is located in the ionization region 9 of the housing 1. In some other embodiments, one or more preconcentrators (not shown) can be located in other regions of the housing 2, for example, in the drift region 13. One advantage of these embodiments is that the dopant can be released instantly, bypassing any tubing, from the preconcentrator(s) to the housing 2.

While the embodiments have been primarily described with respect to an IMS, any suitable device can be used. For example, a mass spectrometer can be provided either in place of the IMS or in combination with an IMS. Any detection apparatus that uses dopants can be employed.

The above described embodiments provide detection systems with a high flexibility in detecting different substances, while the consumption of dopant material is minimized. Advantages are provided, especially if the detection system is configured to be portable, and/or if the dopant is hazardous or expensive.

II. Methods of Analyzing

Another embodiment provides a method of analyzing an analyte substance, comprising supplying a sample suspected of containing the analyte substance, accumulating a dopant in a preconcentrator, such as a MEMS preconcentrator, releasing the dopant from the preconcentrator to an area containing the sample, and determining the detectable species by a detection unit. Optionally, the method further comprises removing the dopant from the system. In some embodiments, such as when an IMS is used to detect the substance, the method further can comprise ionizing the substance to generate detectable species and separating the detectable species. The detection unit can be selected from an ion mobility spectrometer, a mass spectrometer, or a combination thereof, for example.

The sample supplied to the housing can be suspected of containing any substance detectable by the detection unit. For example, the sample can be suspected of containing explosives, drugs, nerve agents, blister agents, or biological agents, such as smallpox, plague, or tularemia.

As explained above, one or more dopants can be added to the system, for example, to reduce the probability of false positive results due to the impurities having low electron or low proton affinity, and/or to shift interfering ion peaks away from a position close to a peak produced by the compound of interest. Accordingly, dopant can be added before, during, or after the sample is ionized.

The preconcentrator is supplied with dopant at a first level and can accumulate the dopant. In response to some signal, the preconcentrator can release the dopant at a level greater than the first level, as described above. This allows the dopant to be added rapidly which, in turn, can improve the speed or ability to detect the substance of interest. In some embodiments, a plurality of preconcentrators can be used to release one or more dopants at the same or varying levels. The preconcentrator can release dopant at regular intervals or in response to specific events, such as a specific detection output. The type of dopant to be released can be predetermined or selected based on the detection results.

The method can be employed using any suitable detection system or combination of detection systems. For sake of clarity, the detection system as shown in FIG. 1 is used below as a non-limiting example for describing an embodiment of the method of analyzing.

As exemplified in FIG. 2, a sample to be analyzed can be supplied to the housing 1 through the sample inlet 3. Molecules contained in the sample can then be ionized in the ionization region 9, and admitted into the drift region 13, through the gating grid 10 that controls the passage of ionized molecules into the drift region 13.

The molecules can be ionized by any suitable methods, for example, but not limited to, radioactive ionization, UV ionization, or corona discharge. The ionized molecules can then drift to the opposite end of the housing 1 at, and be detected by the detection unit 40. The ions can then be identified by their residence time in the drift region 13, which can be, for example, their time of flight.

Such a dopant can be provided by the source unit 12 at a first level that is below a minimum level required for a substantial effect on the detection, and then be accumulated to the preconcentrator 21. Further, at least a portion of the dopant accumulated to the preconcentrator 21 can be released to the housing 2 at selected times, at a second level. The dopant existing in the housing 2 at the second level can have a detectable, and optionally, a substantial effect on the detection. In one embodiment, the second level is significantly higher than the first level, for example, 100 to 4000 times or 400 to 1000 times higher than the first level.

The step of releasing the dopant can comprise releasing the dopant from the preconcentrator into one or more regions of the housing selected from ionization region, a drift region, or a combination thereof.

The releasing of the accumulated dopant from the preconcentrator 21 can be controlled by a signal, such as, for example, an electrical signal. For example, when a trigger signal is received, the preconcentrator 21 can be turned on, releasing at least a part of the accumulated dopant as a short burst of vapor into the housing 2, and, when a trigger signal is not received, the preconcentrator 21 is turned off, not releasing the dopant.

The preconcentrator 21 can be set to receive a trigger signal at any suitable interval, for example, every minute or any other suitable time intervals, after a sufficient amount of the dopant has accumulated to the preconcentrator surface. Alternatively, a trigger signal to turn on the preconcentrator can be supplied by the processing unit 4 only when an ambiguous signal, that could be resolved by the addition of the dopant, is obtained by the detection unit 40.

The dopant circulating in the system can be removed by the removing means 11 so that the system reverts to an un-doped state. In these embodiments, a continuous gas flow can be desired and can be provided by the pump 7 as shown in FIG. 1. The drift gas mixture containing the added dopant flows out through the gas outlet to the tubing 8, and in turn, to the inlet of the pump 7. Next, the gas mixture flows out from the pump to the removing meanings 11, which removes the dopant and other impurities, such as water vapor. The cleaned, dried drift gas can be then supplied to source unit 12, and, in turn, the preconcentrator 21 and the housing 2.

In some embodiments, the method comprises accumulating and releasing more than one dopants. In these embodiments, one more multiple preconcentrators can be used to supply the dopants to the housing in an analogous way.

The above embodiments enable a dopant to be released only when required, and to be removed rapidly when not required. For example, the systems could be arranged to operate initially in an un-doped state, and to trigger the preconcentrator to release a dopant enabling a better identification of the substance only when the identification of a substance is ambiguous.

The foregoing details description has described only a few of the many possible implementations of the systems and methods described herein. For this reason, this detailed description is intended by way of illustration, and not by way of limitations. Variations and modifications of the embodiments disclosed herein can be made based on the description set forth herein, without departing from the scope and spirit of the invention.

What is claimed is:

1. A method of analyzing a substance, comprising:
supplying a sample suspected of containing a substance;
accumulating a dopant in a preconcentrator;
turning the preconcentrator on and off at selected times to cause dopant to be selectively released from the preconcentrator to an area containing the sample, the preconcentrator being operable to release the dopant to the area when the preconcentrator is turned on and to not release the dopant to the area when the preconcentrator is turned off;
ionizing the sample to generate detectable species;
separating the detectable species; and
determining whether the sample contains the substance.

2. The method according to claim 1, further comprising removing the dopant.

3. The method according to claim 1, wherein the preconcentrator is configured to be turned on or off by an electrical signal in such a way that, when the preconcentrator is on, the preconcentrator releases the dopant as a short burst of vapor.

4. The method according to claim 3, wherein the step of determining whether the sample contains the substance comprises processing data outputted by a detection unit and determining whether dopant should be released from the preconcentrator.

5. The method according to claim 1, wherein the preconcentrator is located inside a housing.

6. The method according to claim 1, wherein releasing the dopant comprises releasing the dopant from the preconcentrator into one or more regions of a housing selected from an ionization region, a drift region, or a combination thereof.

7. The method according to claim 1, further comprising releasing a second dopant from a second preconcentrator.

8. The method according to claim 1, wherein the preconcentrator comprises a microelectromechanical system (MEMS) configured to accumulate or release the dopant.

* * * * *